United States Patent [19]

Koshino et al.

[11] Patent Number: 4,978,653
[45] Date of Patent: Dec. 18, 1990

[54] DERIVATIVE OF 2-CYCLOHEXYLPROPANAL AND PERFUMERY COMPOSITION COMPRISING THE SAME

[75] Inventors: Junji Koshino; Yoshiaki Fujikura, both of Utsunomiya; Manabu Fujita, Kashiwa; Nao Toi, Sakura, all of Japan

[73] Assignee: Kao Corporation, Tokyo, Japan

[21] Appl. No.: 400,018

[22] Filed: Aug. 29, 1989

[30] Foreign Application Priority Data

Sep. 1, 1988 [JP] Japan .................. 63-219128

[51] Int. Cl.$^5$ .................................. A61K 7/46
[52] U.S. Cl. ...................... 512/21; 512/22; 512/12; 568/591; 560/35; 549/429; 549/357; 564/253
[58] Field of Search .......... 568/591; 560/35; 504/253; 549/429, 357; 512/21, 12, 22

[56] References Cited

U.S. PATENT DOCUMENTS

| | | | |
|---|---|---|---|
| 2,184,526 | 12/1939 | Meuly | 568/591 |
| 4,372,880 | 2/1983 | Upadek et al. | 512/12 |
| 4,548,743 | 10/1985 | Sprecker et al. | 568/591 |

FOREIGN PATENT DOCUMENTS 3004661  8/1981  Fed. Rep. of Germany ........ 512/12

OTHER PUBLICATIONS

Gros et al., Index Chemicus, 25, #81361 (1967).

Primary Examiner—James H. Reamer
Attorney, Agent, or Firm—Oblon, Spivak, McClelland, Maier & Neustadt

[57] ABSTRACT

2-Cyclohexylpropanal derivatives are disclosed. The derivatives are represented by the following formula (I):

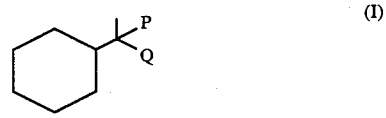

wherein P is a hydrogen atom and Q represents a group —CH=N—OH or a group —CH(OR)$_2$, wherein each R represents a lower alkyl group or two R's together form a lower alkylene group which may have a lower alkyl substituent, or P and Q together form a group

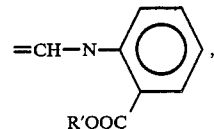

wherein R' is a lower alkyl group.

The compounds possess floral, fruity, or green odors and are useful for preparing perfume compositions.

4 Claims, No Drawings

DERIVATIVE OF 2-CYCLOHEXYLPROPANAL AND PERFUMERY COMPOSITION COMPRISING THE SAME

BACKGROUND OF THE INVENTION

1. Field of the Invention:

The present invention relates to novel compounds having odors, and, more particularly, to derivatives of 2-cyclohexylpropanal and a perfumery composition comprising the same.

There are many useful compounds having odors among acetal derivatives of aromatic aldehyde. In contrast, few compounds are known useful as perfume substance among acetal derivatives having a saturated, cyclohexyl group. For instance, *Fragrance Chemicals II* by O. Okuda, page 1019 (Hirokawa Publishing Co., Tokyo, Japan), outlines, in the chapter of acetal compounds, about 50 acetal compounds having phenyl groups, while the chapter lists only one acetal compound having cyclohexyl group.

Odors of compounds completely differ depending on their chemical structures. Their tenacity and vaporization characteristic also vary depending on the chemical structures. Because of this, synthesizing various compounds and investigating their fragrance is a very important task for the development of new perfume.

In view of the fact that acetal compounds having a cyclohexyl group can readily be synthesized by hydrogenation of the corresponding phenyl acetal compounds and that the hydrogenated acetal compounds can easily be converted into other aldehyde derivatives via an aldehyde, the present inventors have synthesized various aldehyde derivatives having a cyclohexyl group and investigated their odors. As a result the inventors have found that 2-cyclohexyl-propanal derivatives having the formula (I) hereinbelow specified possess floral, fruity, or green odor and are useful as perfume. Such a finding has led to the completion of the present invention.

SUMMARY OF THE INVENTION

Accordingly, an object of this invention is to provide 2-cyclohexylpropanal derivatives represented by the following formula (I):

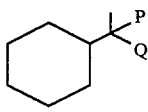
(I)

wherein P is a hydrogen atom and Q represents a group —CH=N—OH or a group —CH(OR)$_2$, wherein each R represents a lower alkyl group or two R's together form a lower alkylene group which may have a lower alkyl substituent, or P and Q together form a group

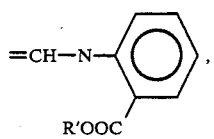

wherein R' is a lower alkyl group; and also to provide a perfumery composition comprising such a 2-cyclohexylpropanal derivative.

Other objects, features and advantages of the invention will hereinafter become more readily apparent from the following description.

DETAILED DESCRIPTION OF THE INVENTION AND PREFERRED EMBODIMENTS

A lower alkyl group in this invention is defined to include linear or branched alkyl groups having a carbon atom content of 1-6. Specific examples are methyl-, ethyl-, n-propyl-, iso-propyl-, n-butyl, iso-butyl-, pentyl, hexyl, etc.

The compounds of the present invention can be prepared by either of the following processes:

Process (A):

2-Phenylpropanal (II) is converted by the reaction with diol compound (III) into an acetal compound of the formula (IVa). This compound (IVa) is hydrogenated to produce the compound of this invention (Ia).

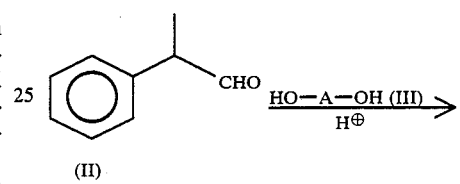

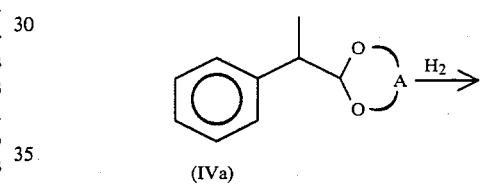

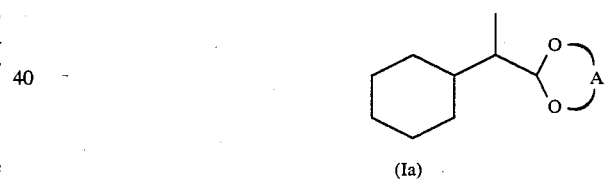

In the formula, A represents a lower alkylene group which may have a C$_1$-C$_3$ lower alkyl substituent.

Preparation of the acetal compound (IVa) is carried out by the reaction of 2-phenylpropanal (II) and a diol compound (III) in the presence of an acid catalyst.

Ethylene glycol, propylene glycol, hexylene glycol, or the like is used as a diol compound (III) in an amount of 1-10 equivalent to 2-phenylpropanal. 0.001-0.1 equivalent amount of sulfuric acid or p-toluene sulfonic acid is used as an acid catalyst. It is desirable to use a solvent such as benzene or toluene for azeotropically evaporating the water produced in the reaction.

An acetal compound of 2-phenylpropanal (IVa) thus produced is then hydrogenated using 0.001-0.1 equivalent of Raney nickel, platinum, palladium, or ruthenium catalyst under a hydrogen pressure of 10-200 atm at a temperature of 80°-200° C. to produce the compound of this invention (Ia).

Process (B):

2-Phenylpropanal (II) is converted by the reaction with a lower alcohol (IIIb) into an acetal compound of the formula (IVb). The compound (IVb) is hydrogenated to produce the compound of this invention (Ib).

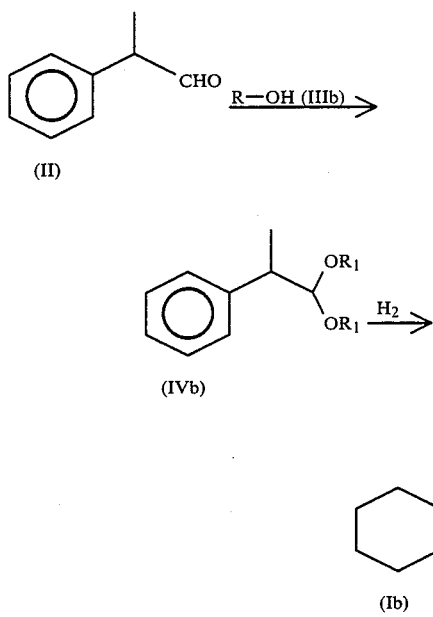

wherein R₁ is a lower alkyl group.

When propanol or the like is used as a lower alcohol (IIIb), the reaction of Process (A) may be utilized. When methanol, ethanol, or the like is used as a lower alcohol (IIIb), however, these lower alcohols are first converted into methyl or ethyl orthoformate, and 1-5 equivalent amount of the methyl or ethyl orthoformate is used together with a 0.01-1 equivalent amount of ammonium chloride as a catalyst.

Process (C):

2-Cyclohexylpropanal (V) is acetalized to produce the compound of this invention (Ia) or (Ib) according to the following reaction:

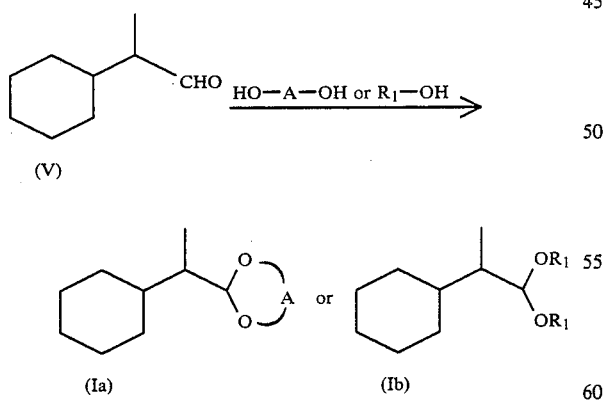

wherein R₁ is a lower alkyl group.

Cyclohexylpropanal (V) which is the raw material can easily be prepared by hydrolysis of ethylene acetal or oxidation of 2-cyclohexylpropanol. The acetalization reaction can be carried out according to the conditions of Process (A) or (B).

Process (D):

2-Cyclohexylpropanal (V) is oximized to produce the compound of this invention (Ic) according to the following reaction:

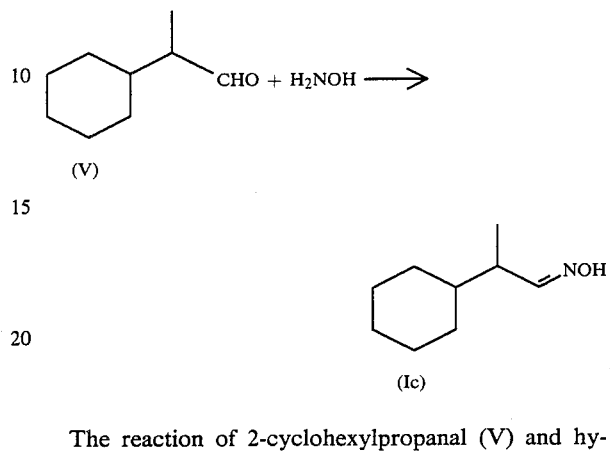

The reaction of 2-cyclohexylpropanal (V) and hydroxyl amine to produce oxime is carried out using 1.0-1.5 equivalent of sulfate or chloride of hydroxyl amine for 1 equivalent of compound (V) in a mixed solvent, for example, of ethanol and an aqueous solution of sodium carbonate, potassium carbonate, sodium acetate, potassium acetate, sodium hydroxide, or potassium hydroxide.

Process (E):

2-Cyclohexylpropanal (V) and an anthranillic acid ester (VI) are reacted to produce the compound of this invention (Id) according to the following reaction:

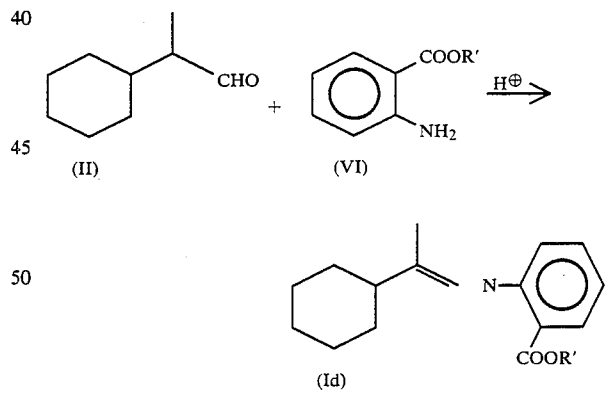

wherein R' is a lower alkyl group.

The reaction is carried out using 1.0-1.5 equivalent of methyl anthranilate for 1 equivalent of 2-cyclohexylpropanal (V) in the presence of a 0.01-0.1 equivalent amount of sulfuric acid or p-toluene sulfonic acid as an acid catalyst. Benzene or toluene is used as a solvent and compound (Id) is produced while azeotropically evaporating the water produced in the reaction.

The compounds of the present invention prepared according to the above processes have odors shown in Table 1.

TABLE 1

| Compound Nos. | Odors |
|---|---|
| Compound No. 1 — cyclohexyl-CH(CH₃)-CH(O-CH₂-CH₂-O) (1,3-dioxolane) | Fruity, honey, waxy, isononylacetate-like |
| Compound No. 2 — cyclohexyl-CH(CH₃)-CH(O-CH₂-CH₂-CH₂-O) (1,3-dioxane) | Fruity, green, floral, jasmin-like |
| Compound No. 3 — cyclohexyl-CH(CH₃)-CH(O-CH₂-C(CH₃)₂-CH₂-O) | Floral, green, hyacinth |
| Compound No. 4 — cyclohexyl-CH(CH₃)-CH(OMe)₂ | Green, floral, fruity, woody |
| Compound No. 5 — cyclohexyl-CH(CH₃)-CH(OEt)₂ | Fruity, peach, strawberry-like, |
| Compound No. 6 — cyclohexyl-CH(CH₃)-CH(OPr)₂ | Green, floral, amylsalicylate-like |
| Compound No. 7 — cyclohexyl-CH(CH₃)-CH=NOH | Minty, woody, green, |
| Compound No. 8 — cyclohexyl-C(=CH₂)-N(H)-C₆H₄-COOMe | Soft, sweet floral, weak green |

As fully discussed above, the compounds (I) of the present invention possess odors. Since such odors are tenacious, the compounds can be used for a wide variety of products which require odors or fragrances such as perfume, soap, shampoos, rinses, detergents, cosmetics, sprays, aromas, and the like.

Other features of the invention will become apparent in the course of the following description of the exemplary embodiments which are given for illustration of the invention and are not intended to be limiting thereof.

EXAMPLES

Example 1

Synthesis of 2-cyclohexylpropanal ethyleneacetal (Compound No. 1)

(i) Into a 1 liter round bottom flask equipped with a Deanstark dehydrator 400 ml of toluene, 250 g of 2-phenylpropanal (II), 170 g of ethylene glycol, and 1.0 g of p-toluene sulfonic acid were charged. The mixture was stirred under refluxing toluene for 6 hours, during which 38 ml of water was removed. After washing with water, toluene was evaporated from the resulting reaction product. The residue was distilled under reduced pressure to prepare 304 g of 2-phenylpropanal ethyleneacetal (purity: 98.8%, boiling point: 100° C./5 mmHg).

(ii) 300 g of the product prepared in (i) above and 3 g of 5% Ru/C catalyst was placed in a 1 liter autoclave and hydrogenation was performed at a temperature of 120° C. and a hydrogen pressure of 50 kg/cm$^2$ for 12 hours. After removing the catalyst by filtration, the reaction mixture was distilled under reduced pressure to produce 304 g of 2-cyclohexylpropanal ethyleneacetal (Compound No. 1; purity: 99.3%, boiling point: 99.5° C./5 mmHg). The compound was a colorless, transparent liquid having a fruity, honey, waxy, and isononylacetate-like odor.

The results of IR and NMR analyses of 2-phenylpropanal ethyleneacetal and 2-cyclohexylpropanal ethyleneacetal were as follows:

2-phenylpropanal ethyleneacetal
IR (film): 1035, 1062, 1089, 1458, 1497, 2884, 2974, 3028 cm$^{-1}$
NMR (60 MHz, CDCl$_3$): 1.30 (d, J=7 Hz, 3H), 2.90 (m, 1H), 3.80 (s, 4H), 4.90 (d, J=4 Hz, 1H), 7.20 (s, 5H) ppm 2-cyclohexylpropanal ethyleneacetal
IR (film): 1065, 1098, 1455, 2926 cm$^{-1}$
NMR (60 MHz, CDCl$_3$) 0.87 (d, J=7 Hz, 3H), 0.93–1.90 (m, 12H), 3.73–4.03 (m, 4H), 4.80 (d, J=5 Hz, 1H) ppm Example 2

Synthesis of 2-cyclohexylpropanal propyleneglycolacetal (Compound No. 2)

(i) 100.0 g of a compound (Ia) was hydrogenated in a solution of 2 g of p-toluene sulfonic acid, 200 ml of acetone, and 500 ml of water at 60° C. for 24 hours. The hydrogenated product was distilled to obtain 66.5 g of 2-cyclohexylpropanal (purity: 98.5%, boiling point: 65° C./5 mmHg).

(ii) 30.0 g of the compound produced in (i) above was reacted with 24.4 g of propylene glycol under the same conditions as in (ii) of Example 1 to produce 36.8 g of Compound No. 2 (purity: 99.5%, boiling point: 102° C./5 mmHg). The compound was a colorless, transparent liquid having a fruity, green, floral, and jasmin-like odor.

The results of IR and NMR analyses of 2-phenylpropanal propyleneglycolacetal were as follows:
IR (film): 1059, 1101, 1383, 1410, 2926, cm$^{-1}$
NMR (60 MHz, CDCl$_3$): 0.88 (d, J=7 Hz, 3H), 0.90–1.90 (m, 15H), 3.23–3.55 (m, 1H), 3.80–4.38 (m, 2H), 4.81–5.03 (m, 1H)

Example 3

Synthesis of 2-cyclohexylpropanal hexyleneglycolacetal (Compound No. 3)

30.0 g of 2-cyclohexylpropanal was reacted with 37.8 g of hexylene glycol under the same conditions as in (ii) of Example 1 to produce 48.3 g of Compound No. 3 (purity: 99.5%, boiling point: 106° C./5 mmHg). The compound was a colorless, transparent liquid having a floral, green, and hyacinth odor.

The results of IR and NMR analyses of 2-phenylpropanal hexyleneglycolacetal were as follows:
IR (film): 1029, 1098, 1170, 1377, 1452, 2926 cm$^{-1}$
NMR (60 MHz, CDCl$_3$) 0.86 (d, J=7 Hz, 3H), 0.90–1.88 (m, 23H), 3.48–4.12 (m, 1H), 4.65 (d, J=4 Hz, 1H) ppm Example 4

Synthesis of 2-cyclohexylpropanal dimethylacetal (Compound No. 4)

Into a 200 ml round bottom flask 50 ml of methanol, 30.0 g of 2-cyclohexylpropanal, 36.1 g of methyl orthoformate, and 0.5 g of ammoniumchloride were charged and the mixture was stirred at room temperature for 12 hours. After washing the resulting reaction mixture with water, the residue was distilled to prepare 37.5 g of Compound No. 4 (purity: 99.3%, boiling point: 83° C./5 mmHg). The compound was a colorless, transparent liquid having a floral and fruity odor.

The results of IR and NMR analyses of 2-phenylpropanal dimethylacetal were as follows:
IR (film): 1068, 1107, 1455, 2687, 2926 cm$^{-1}$
NMR (60 MHz, CDCl$_3$): 0.83 (d, J=7 Hz, 3H), 0.86–1.93 (m, 12H), 3.35 (s, 6H), 4.18 (d, J=7 Hz, 1H) ppm Example 5

Synthesis of 2-cyclohexylpropanal diethylacetal (Compound No. 5)

An acetalization reaction was carried out in the same manner as in Example 4, except that instead of methanol and methyl orthoformate, 50 ml of ethanol and 50.4 g of ethyl orthoformate were used, to produce 41.4 g of Compound No. 5 (purity: 98.7%, boiling point: 102° C./5 mmHg). The compound was a colorless, transparent liquid having a fruity, peach, and strawberry-like odor.

The results of IR and NMR analyses of 2-phenylpropanal diethylacetal were as follows:
IR (film): 1065, 1116, 1377, 1452, 2926 cm$^{-1}$
NMR (60 MHz, CDCl$_3$): 0.83 (d, J=7 Hz, 3H), 1.20 (d, J=7 Hz, 6H), 0.90–1.93 (m, 12H), 3.30–3.83 (m, 4H), 4.30 (d, J=7 Hz, 1H) ppm Example 6

Synthesis of 2-cyclohexylpropanal dipropylactal (Compound No. 6)

An acetalization reaction was carried out in the same manner as in Example 1 using 30.0 g of 2-cyclohexylpropanal and using, instead of ethylene glycol and toluene, 39.1 g of propanol and 100 g of benzene to produce 46.3 g of Compound No. 6 (purity: 98.5%, boiling point: 114° C./5 mmHg). The compound was a colorless, transparent liquid having a green, floral, amylsalicylate-like odor.

The results of IR and NMR analysis of 2-phenylpropanal dipropylacetal were as follows:
IR (film): 1038, 1071, 1113, 1455, 2968 cm$^{-1}$
NMR (60 MHz, CDCl$_3$) 0.85 (d, J=7 Hz, 3H), 0.95 (t, J=7 Hz, 6H), 1.0–2.0 (m, 16H), 3.40 (t, J=7 Hz, 4H), 4.31 (d, J=7 Hz, 1H) ppm Example 7

Synthesis of 2-cyclohexylpropanal oxime (Compound No. 7)

(i) Into a 200 ml round bottom flask 10 ml of ethanol, 30.0 g of 2-cyclohexylpropanal, and 32.1 g of a 50% aqueous solution of hydroxylamine hydrochloride were charged. After a dropwise addition of 76.7 g of a 30% aqueous solution of sodium carbonate, the mixture was stirred at room temperature for 2 hours. 200 ml of ether was added to the reaction mixture, and, after washing with water, the mixture was distilled to obtain 30.4 g of Compound No. 7 (purity: 98.9%, boiling point: 108° C./5 mmHg). The compound was a colorless, transparent liquid having a minty, woody, and green odor.

The results of IR and NMR analyses of and 2-cyclohexylpropanal oxime were as follows:

IR (film): 957, 1455, 1497, 2932, 3256 cm$^{-1}$

NMR (60 MHz, CDCl$_3$) 0.80–3.35 (m, 15H), 6.57 (d, J=8 Hz, 0.3H), 7.33 (d, J=8 Hz, 0.7H), 7.8–9.4 (m, 1H) ppm

Example 8

Synthesis of 2-cyclohexylpropanal methyl anthranilate enamine (Compound No. 8)

(i) Into a 300 ml round bottom flask equipped with a Deanstark dehydrator 100 ml of toluene, 30.0 g of 2-cyclohexylpropanal, 37.8 g of methyl anthranilate, and 0.1 g of p-toluene sulfonic acid were charged. The mixture was stirred under refluxing toluene for 6 hours, during which 3.7 ml of water was removed. After washing with water, toluene was evaporated from the resulting reaction product. The residue was distilled under reduced pressure to prepare 49.5 g of 2-cyclohexylpropanal methyl anthranilate enamine (purity: 98.2%, boiling point: 165° C./0.2 mmHg). The compound was a reddish-orange colored, transparent liquid having a soft, sweet floral and weak green odor.

The results of IR and NMR analyses of 2-cyclohexylpropanal methyl anthranilate enamine were as follows:

IR (film): 747, 1083, 1518, 1584, 1665, 1692, 2926, 3328 cm$^{-1}$

NMR (60 MHz, CDCl$_3$): 0.90–2.10 (m, 15H), 3.88 (s, 3H), 6.0–7.5 (m, 4H)

Example 9

Gardenia-type Perfumery Composition:

| | | |
|---|---|---|
| Styrallyl acetate | 50 | parts by weight |
| Benzyl acetate | 100 | |
| Hydroxycitronellal | 200 | |
| Phenylethyl alcohol | 150 | |
| Linalool | 100 | |
| Heliotropine | 40 | |
| τ-Nonalactone | 20 | |
| α-Ionone | 80 | |
| Cinnmic alcohol | 40 | |
| Dimethylbenzyl carbinol | 60 | |
| Indole | 5 | |
| cis-Jasmone | 5 | |
| | 850 | |

A gardenia-type perfume was prepared by blending 850 parts by weight of the above components and 150 parts by weight of 2-cyclohexylpropanal diethyleneacetal (Compound No. 5). The perfume possessed a natural, green-fruity odor.

Example 10

Peach-type Perfumery Composition:

| | | |
|---|---|---|
| Ethyl valerate | 100 | parts by weight |
| Ethyl hexanoate | 50 | |
| Amyl acetate | 60 | |
| Amyl butylate | 30 | |
| Benzaldehyde | 10 | |
| τ-undecanelactone | 400 | |
| α-undecanelactone | 50 | |
| Vanillin | 200 | |
| | 900 | |

A peach-like perfume was prepared by blending 900 parts by weight of the above components and 100 parts by weight of 2-cyclohexylpropanal methyl anthranilate enamine (Compound No. 8). The perfume possessed a fresh, green-fruity odor.

Obviously, numerous modifications and variations of the present invention are possible in light of the above teachings. It is therefore to be understood that within the scope of the appended claims, the invention may be practiced otherwise than as specifically described herein.

What is claimed is:

1. A 2-cyclohexylpropanal derivative represented by the following formula (I):

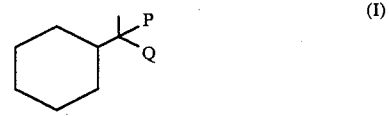

wherein P is a hydrogen atom and Q represents a group —CH=N—OH or a group —CH(OR)$_2$, wherein each R represents a C$_1$–C$_3$ lower alkyl group or two R's together form a lower alkylene group which may have at least one lower alkyl group which may have at least one lower alkyl substituent, wherein the total carbon atom content of two R's is 2–6, or R and Q together form a group

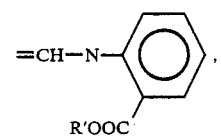

wherein R' is a C$_1$–C$_2$ lower alkyl group.

2. A perfumery composition comprising a 2-cyclohexylpropanal derivative represented by the following formula (I):

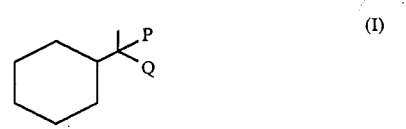

wherein P is a hydrogen atom and Q represents a group —CH=N—OH or a group —CH(OR)$_2$, wherein each R represents a C$_1$–C$_3$ lower alkyl group or two R's together from a lower alkylene group which may have at least one lower alkyl group which may have at least one lower alkyl substituent wherein the total carbon atom content of two R's is 2–6, or P and Q together form a group

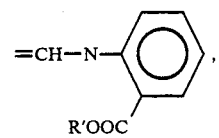

wherein R' is a C$_1$–C$_2$ lower alkyl group and conventional additives.

3. A 2-cyclohexylpropanal derivative according to claim 1, wherein in the formula (1) P and Q together form a group
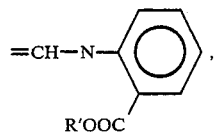
wherein R' is a $C_1$–$C_2$ lower alkyl group.
4. A perfumery composition according to claim 2, wherein in the 2-cyclohexylpropanal derivative of formula (I) P and Q together form a group
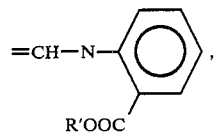
wherein R' is a $C_1$–$C_2$ lower alkyl group and conventional additives.
* * * * *